US006944338B2

(12) United States Patent
Lock et al.

(10) Patent No.: US 6,944,338 B2
(45) Date of Patent: Sep. 13, 2005

(54) SYSTEM FOR IDENTIFYING CLUSTERS IN SCATTER PLOTS USING SMOOTHED POLYGONS WITH OPTIMAL BOUNDARIES

(75) Inventors: Michael D. Lock, Mountain View, CA (US); Sunil S. Dalal, Hayward, CA (US); Ilya Gluhovsky, Mountain View, CA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 717 days.

(21) Appl. No.: 09/853,037

(22) Filed: May 11, 2001

(65) Prior Publication Data

US 2002/0029235 A1 Mar. 7, 2002

Related U.S. Application Data

(60) Provisional application No. 60/203,515, filed on May 11, 2000, provisional application No. 60/203,590, filed on May 11, 2000, provisional application No. 60/203,585, filed on May 11, 2000, and provisional application No. 60/203,577, filed on May 11, 2000.

(51) Int. Cl.⁷ ............................. G06K 9/00; G06K 9/62
(52) U.S. Cl. ...................................... 382/168; 382/225
(58) Field of Search ............................... 382/128, 133, 382/168, 170, 171, 173, 189, 199, 224, 225, 266; 436/63

(56) References Cited

U.S. PATENT DOCUMENTS

| | | | |
|---|---|---|---|
| 4,207,554 A | * 6/1980 | Resnick et al. ............. | 382/133 |
| 4,599,307 A | 7/1986 | Saunders et al. ............. | 435/34 |
| 4,661,913 A | 4/1987 | Wu et al. ................... | 364/500 |
| 4,704,891 A | 11/1987 | Recktenwald et al. ........ | 73/1 R |
| 4,727,020 A | 2/1988 | Recktenwald ................. | 435/6 |
| 4,745,285 A | 5/1988 | Recktenwald et al. ... | 250/458.1 |
| 4,987,086 A | 1/1991 | Brosnan et al. ............. | 436/501 |
| 5,018,088 A | 5/1991 | Higbie ....................... | 364/574 |
| 5,314,824 A | 5/1994 | Schwartz ..................... | 436/10 |

(Continued)

OTHER PUBLICATIONS

Haynes, J.L., "Principles of Flow Cytometry", Cytometry Supplement, 3:7–17 (1988).

Young, Ian T. et al., "Recursive Implementation of the Gaussian Filter", Signal Processing 44, pp. 139–151 (1995).

Koontz, Warren L.G. et al., "A Nonparametric Valley–Seeking Technique for Cluster Analysis", IEEE Transactions on Computers, vol. C–21, No. 2, Feb. 1972, pp. 171–178.

Whyatt, J.D. et al., "The Douglas–Peucker Line Simplification Algorithm", SUC Bulletin vol. 22 No. 1, pp. 17–25 (1988).

(Continued)

Primary Examiner—Andrew W. Johns
Assistant Examiner—Amir Alavi
(74) Attorney, Agent, or Firm—Roylance, Abrams, Berdo & Goodman, L.L.P.

(57) ABSTRACT

An apparatus and method for identifying clusters in two-dimensional data by generating a two-dimensional histogram characterized by a grid of bins, determining a density estimate based on the bins, and identifying at least one cluster in the data. A smoothed density estimate is generated using a Gaussian kernel estimator algorithm. Clusters are identified by locating peaks and valleys in the density estimate (e.g., by comparing slope of adjacent bins). Boundaries (e.g., polygons) around clusters are identified using bins after bins are identified as being associated with a cluster. Boundaries can be simplified (e.g., by reducing the number of vertices in a polygon) to facilitate data manipulation.

33 Claims, 12 Drawing Sheets

U.S. PATENT DOCUMENTS

| | | | |
|---|---|---|---|
| 5,365,472 A | | 11/1994 | Solka et al. ................. 364/807 |
| 5,445,939 A | | 8/1995 | Anderson .................. 435/7.24 |
| 5,465,321 A | | 11/1995 | Smyth .......................... 395/22 |
| 5,528,494 A | | 6/1996 | Moses ......................... 364/420 |
| 5,548,661 A | * | 8/1996 | Price et al. ................. 382/133 |
| 5,572,597 A | | 11/1996 | Chang et al. ............... 382/125 |
| 5,627,040 A | | 5/1997 | Bierre et al. ............... 435/7.24 |
| 5,757,954 A | * | 5/1998 | Kuan et al. ................. 382/133 |
| 5,768,413 A | | 6/1998 | Levin et al. ................ 382/173 |
| 5,776,709 A | | 7/1998 | Jackson et al. ............ 435/7.24 |
| 5,991,028 A | * | 11/1999 | Cabib et al. ................ 356/456 |
| 6,007,996 A | * | 12/1999 | McNamara et al. ........... 435/6 |
| 6,014,904 A | * | 1/2000 | Lock ......................... 73/865.5 |
| 6,115,488 A | | 9/2000 | Rogers et al. .............. 382/132 |
| 6,148,096 A | * | 11/2000 | Pressman et al. .......... 382/133 |
| 6,226,409 B1 | | 5/2001 | Cham et al. ................ 382/228 |
| 6,246,972 B1 | | 6/2001 | Klimasauskas ............... 703/2 |
| 6,317,517 B1 | * | 11/2001 | Lu ............................. 382/228 |
| 6,372,506 B1 | * | 4/2002 | Norton ......................... 436/63 |
| 6,620,591 B1 | * | 9/2003 | Dunlay et al. ............... 435/7.2 |
| 6,687,395 B1 | * | 2/2004 | Dietz et al. ................. 382/133 |

OTHER PUBLICATIONS

Douglas D.H. et al., "Algorithms for the Reduction of the Number of Points Required to Represent a Digitized Line or its Caricature", *The Canadian Cartographer* 10(2):112–122 (1973).

Press, W.H. et al., "Numerical Recipes in Fortran, Second Edition", Cambridge University Press, pp. 436–448 (1992).

Jones, M.C. et al., "A Brief Survey of Bandwidth Selection for Density Estimation" Journal of the American Statistical Association, vol. 91, No. 433, pp. 401–407 (1996).

Koontz, Warren L.G. et al, "A Graph–Theoretic Approach to Nonparametric Cluster Analysis", IEEE Transactions on Computers, vol. C–25, No. 9, pp. 936–946, Sep. 1976.

* cited by examiner

SYSTEM FOR IDENTIFYING CLUSTERS IN SCATTER PLOTS USING SMOOTHED POLYGONS WITH OPTIMAL BOUNDARIES

The present invention claims benefit under 35 U.S.C. § 119(e) of a U.S. Provisional Patent Application of Dwayne Yount et al. entitled "Hardware and Electronics Architecture for a Flow Cyometer", Ser. No. 60/203,515, filed May 11, 2000, of a U.S. Provisional Patent Application of Michael Lock et al. entitled "Cluster Finder Algorithm for Flow Cytometer", Ser. No. 60/203,590, filed May 11, 2000, of a U.S. Provisional Patent Application of Michael Goldberg et al. entitled "User Interface and Network Architecture for Flow Cytometer", Ser. No. 60/203,585, filed May 11, 2000 and of a U.S. Provisional Patent Application of John Cardott et al. entitled "Digital Flow Cytometer", Ser. No. 60/203,577, filed May 11, 2000, the entire contents of each of said provisional patent applications being incorporated herein by reference.

CROSS-REFERENCE TO RELATED APPLICATIONS

Related subject matter is disclosed in a copending U.S. Patent Application of Pierce O. Norton entitled "Apparatus and Method for Verifying Drop Delay in a Flow Cytometer", Ser. No. 09/346,692, filed Jul. 2, 1999, in a copending U.S. patent application of Kenneth F. Uffenheimer et al. entitled "Apparatus and Method for Processing Sample Materials Contained in a Plurality of Sample Tubes", Ser. No. 09/447,804, filed Nov. 23, 1999, and in a copending U.S. patent application of Dwayne Yount et al. entitled "A System and Method for Providing Improved Event Reading and Data Processing Capabilities in a Flow Cytometer", Ser. No. 10/953,677, filed even date herewith, the entire contents of each of these applications are incorporated herein by reference.

BACKGROUND OF THE INVENTION

1. Field of the Invention

The present invention relates generally to a method for locating clusters on a two-dimensional scatter plot by automatically defining a position of at least one variable position, geometric boundary surface on the scatter plot so as to enclose a group of the displayed particles in a data cluster. The boundary surface has a polygonal shape defined by a plurality of vertices about at least one cell cluster. The present invention further relates to generating a cluster using a two-dimensional density estimate whereby the data is binned in a histogram and the bin counts subjected to smoothing. Bins are then assigned to respective clusters whereby clusters are separated by valleys in the density estimate.

2. Description of the Related Art

Flow cytometry, the measurement and/or separation of objects such as cells, nuclei, chromosomes and other particles in a moving liquid stream ("objects"), is well established as a valuable analysis tool in research and clinical laboratories. A discussion of the various principles, techniques and apparatus behind flow cytometry is set forth in an article by John L. Haynes, entitled "Principles of Flow Cytometry", *Cytometry Supplement* 3:7–17 (1988), the disclosure of which is hereby incorporated by reference. Conventional flow cytometry devices for analyzing objects with specific characteristics basically consist of a liquid stream forming a sheath to focus the objects as they pass through an orifice associated with the analyzing or counting capabilities of the device. Usually, this type of analysis includes labeling the objects with one or more markers and then examining them for the presence or absence of one or more such markers. In the case of a cell, such as a leukocyte, tumor cell or microorganism, the marker can be directed to a molecule on the cell surface or to a molecule in the cytoplasm. Examination of a cell's physical characteristics, as well as the presence or absence of particular markers can be used to identify the population to which a cell belongs. Accordingly, there has been considerable interest in flow cytometry to analyze and sort objects. The objects can be analyzed and/or sorted at high speeds to collect tens of thousand of the objects based on a variety of chemical and physical characteristics such as size, granulation of the cytoplasm and presentation of specific antigens.

Flow cytometry comprises a well known methodology using multi-parameter data for identifying and distinguishing between different cell types in a sample. For example, the sample may be drawn from a variety of biological fluids, such as blood, lymph or urine, or may be derived from suspensions of cells from hard tissues such as colon, lung, breast, kidney or liver. In a flow cytometer, cells are passed, in suspension, substantially one at a time through one or more sensing regions where in each region each cell is illuminated by an energy source. The energy source generally comprises an illumination means that emits light of a single wavelength such as that provided by a laser (e.g., He/Ne or argon) or a mercury arc lamp with appropriate filters. Light at 488 nm is a generally used wavelength of emission in a flow cytometer having a single sensing region.

In series with a sensing region, multiple light collection means, such as photomultiplier tubes (or "PMTs"), are used to record light that passes through each cell (generally referred to as forward light scatter), light that is reflected orthogonal to the direction of the flow of the cells through the sensing region (generally referred to as orthogonal or side light scatter) and fluorescent light emitted form the cell, if it is labeled with a fluorescent marker(s), as the cell passes through the sensing region and is illuminated by the energy source. Each of forward light scatter (or "FSC"), orthogonal or side light scatter (or "SSC"), and fluorescence emissions (or "FL1," "FL2," etc.) comprise a separate parameter for each cell (or each "event"). Thus, for example, two, three, four or more parameters can be collected (and recorded) from a cell labeled with two different fluorescence markers. Flow cytometers further comprise data acquisition, analysis and recording means, such as a computer, wherein multiple data channels record data from each PMT for the light scatter and fluorescence emitted by each cell as it passes through the sensing region. The purpose of the analysis system is to classify and count cells wherein each cell presents itself as a set of digitized parameter values. Typically, by current analysis methods, the data collected in real time (or recorded for later analysis) is plotted in 2-D space for ease of visualization.

Such plots are referred to as "scatter plots" or "dot plots" and a typical example of a dot plot drawn from light scatter data recorded for leukocytes is shown in FIG. 1 of U.S. Pat. No. 4,987,086, the disclosure of which is hereby incorporated by reference in its entirety. By plotting orthogonal light scatter versus forward light scatter, one can distinguish between granulocytes, monocytes and lymphocytes in a population of leukocytes isolated from whole blood. By electronically (or manually) "gating" on only lymphocytes using light scatter, for example, and by the use of the appropriate monoclonal antibodies labeled with fluorochromes of different emission wavelength, one can further distinguish between cell types within the lymphocyte population (e.g., between T helper cells and T cytotoxic cells). U.S. Pat. Nos. 4,727,020, 4,704,891, 4,599,307, 4,987,086 and 6,014,904 describe the arrangement of the various components that comprise a flow cytometer, the general principles of use and one approach to gating on cells in order to discriminate between populations of cells in a blood sample. The disclosures of these patents are hereby incorporated by reference in their entireties.

Of particular interest is the analysis of cells from patients infected with HIV, the virus which causes AIDS. It is well known that CD4$^+$ lymphocytes play an important role in HIV infection and AIDS. For example, counting the number of CD4$^+$ T lymphocytes in a sample of blood from an infected individual will provide an indication of the progress of the disease. A cell count under 200 per cubic millimeter is an indication that the patient has progressed from being seropositive to AIDS. In addition to counting CD4$^+$ T lymphocytes, CD8$^+$ T lymphocytes also have been counted and a ratio of CD4:CD8 cells has been used in understanding AIDS.

In both cases, a sample of whole blood is obtained from a patient. Monoclonal antibodies against CD3 (a pan-T lymphocyte marker), CD4 and CD8 are labeled directly or indirectly with fluorescent dye. These dyes have emission spectra that are distinguishable from each other. Examples of such dyes are set forth in Example 1 of U.S. Pat. No. 4,745,285, the disclosure of which is hereby incorporated by reference in its entirety. The labeled cells then are run on the flow cytometer and data is recorded. Analysis of the data can proceed in real time or be stored in list mode for later analysis.

While data analyzed in 2-D space can yield discrete populations of cells, most often the dot plots represent projections of multiple clusters. As a result, often it is difficult to distinguish between cells which fall into regions of apparent overlap between clusters. In such cases, cells can be inadvertently classified in a wrong cluster, and thus, contribute inaccuracy to the population counts and percentages being reported. In blood from an HIV infected patient for example, over-inclusion of T cells as being CD4$^+$ could lead a clinician to believe a patient had not progressed to AIDS, and thus, certain treatment which otherwise might be given could be withheld. In cancers, such as leukemia, certain residual tumor cells might remain in the bone marrow after therapy. These residual cells are present in very low frequencies (i.e., their presence is rare and thus their occurrence in a large sample is a "rare event"), and thus, their detection and classification are both difficult and important.

One known method for solving this problem relies on a gravitational attractor consisting of a geometric boundary surface of fixed size, shape and orientation, but of variable position, and a computational engine by which the boundary surface positions itself optimally to enclose a cluster of multi-parameter events, with multiple attractors for simultaneously classifying multiple clusters of events within the same datastream or recorded data distribution. The strategy is to assign one attractor per population to be identified and/or sorted. This method is described in U.S. Pat. No. 5,627,040, the disclosure of which is hereby incorporated by reference in its entirety. However, there are some limitations to this method. For example, because of the fixed size, shape and orientation of the boundary surface, some cells can be inadvertently classified in a wrong cluster or omitted from inclusion within the boundary, and therefore contribute inaccuracy to the population counts and percentages being reported. Thus, there has been a need for a method for more accurately discriminating between clusters of cells, and therefore for more accurately identifying and/or sorting cells into different populations.

SUMMARY OF THE INVENTION

The present invention provides a cluster finder algorithm that is operable to analyze a sample of two-dimensional data (e.g., obtained via flow cytometry) to locate clusters therein and to define boundaries around the clusters.

In accordance with one aspect of the present invention, the boundaries are polygons and the cluster finder algorithm simplifies a boundary by reducing the number of vertices of the polygon to facilitate manipulation of the corresponding data by a user.

In accordance with another aspect of the present invention, the cluster finder algorithm optimizes identification of cluster boundaries by generating a histogram of the data and then a smoothed density estimate of the histogram, as opposed to processing each of the data points.

In accordance with still another aspect of the present invention, the grid structure imposed on the data by using a histogram facilitates location of peaks and valleys in the density estimate and therefore the identification of clusters in the data, as well as determination of boundaries of clusters.

In accordance with an embodiment of the present invention, a method is provided for identifying clusters in two-dimensional data. The method comprises: (1) generating a two-dimensional histogram characterized by a grid having an x-axis and a y-axis and a selected number of bins in the x-direction and a selected number of bins in the y-direction, and the data comprising n pairs of points $(x_i, y_i)$, i=1, ..., n such that the histogram comprises fewer bins than points; (2) determining a density estimate based on the bins; and (3) identifying at least one cluster in the data. The method can further comprise generating a smoothed density estimate (e.g., by using a Gaussian kernel estimator algorithm). The method of the present invention allows boundaries around clusters to be identified (e.g., as polygons) and simplified (e.g., reducing the number of vertices in a polygon while enclosing approximately the same area within the originally-defined boundary).

In accordance with another of the present invention, clusters are identified as comprising a group of bins in the histogram which are separated from other bins by a valley in the density estimate. The bins can be identified by comparing the slope of each of the bins with that of adjacent bins. Bins that correspond to peaks in the estimate can be assigned respective cluster identification codes, and bins associated with one of the peaks can be assigned the corresponding cluster identification code. The location of a boundary is therefore optimized by analyzing each of the bins to determine if adjacent bins have the same cluster identification code. Bins that have no adjacent bins with data or which have no adjacent bins with the same cluster identification code are used as exterior points for boundary determination.

In accordance with another embodiment of the present invention, the cluster finder algorithm implementing the method described herein is implemented via a programmable processing device. A display provides a visual indication of the plurality of clusters. The processing device is operable to provide a user with the boundary of one of the plurality clusters on the display when selected via a user input device. The processing device can also alter a boundary of a cluster in response to a user commands generated via the user input device. The processing device facilitates batch processing by generating a template after a first data set is gated. The template facilitates processing other related data sets to locate corresponding clusters.

BRIEF DESCRIPTION OF THE DRAWINGS

The various objects, advantages and novel features of the present invention will be more readily appreciated from the following detailed description when read in conjunction with the accompanying drawings, in which.

DETAILED DESCRIPTION OF THE PREFERRED EMBODIMENTS

Figure 1:
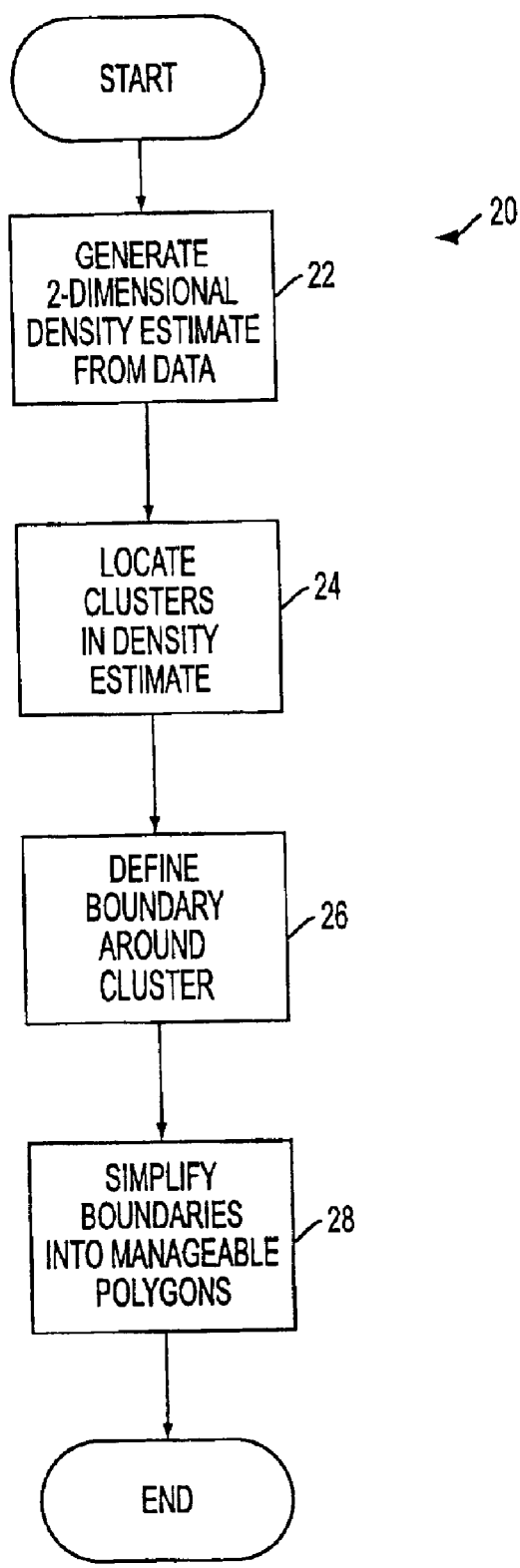
FIG. 1 is a flow chart illustrating a sequence of operations for identifying clusters in scatter plots in accordance with an embodiment of the present invention.

In accordance with an embodiment of the present invention, a cluster finder algorithm 20 is provided which can be used with event data such as scatter plots of data obtained via flow cytometry. The cluster finder algorithm 20 is illustrated in FIG. 1 and will be described in further detail below. It is to be understood that the cluster finder algorithm 20 can be used with essentially any application employing a two-dimensional data set.

Figure 2:
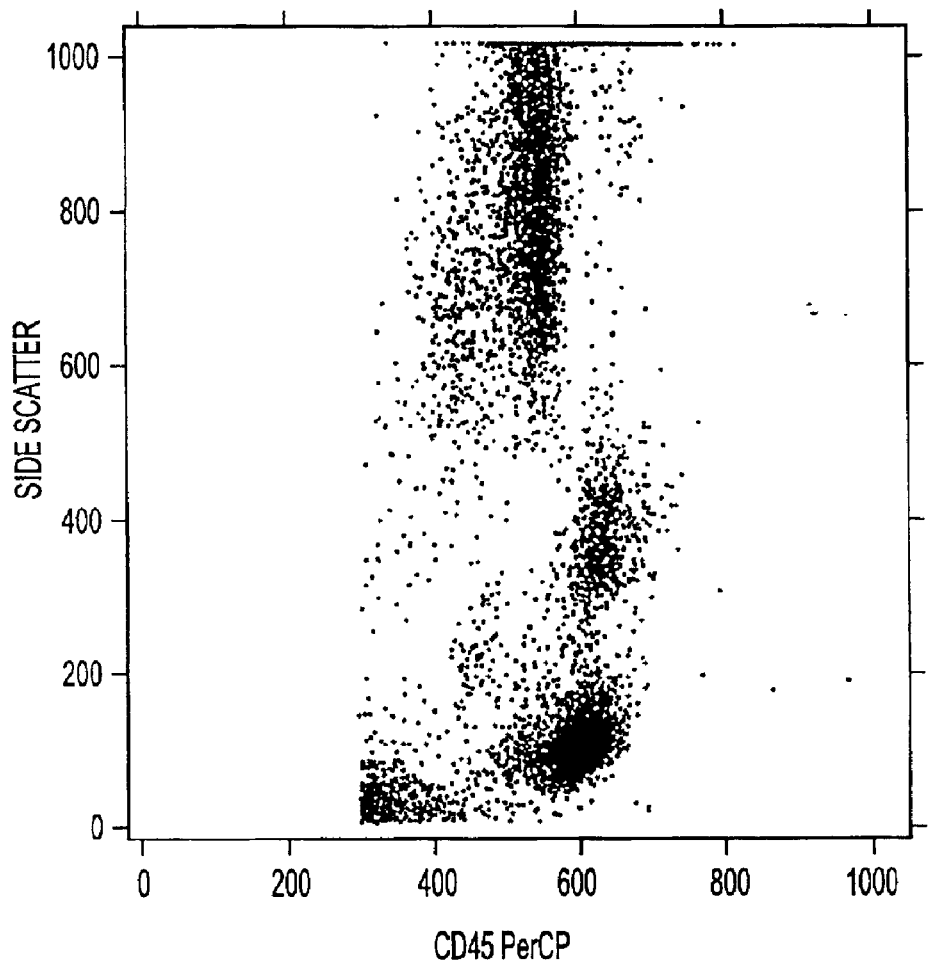
FIG. 2 is an exemplary two-dimensional scatter plot.
Figure 11:
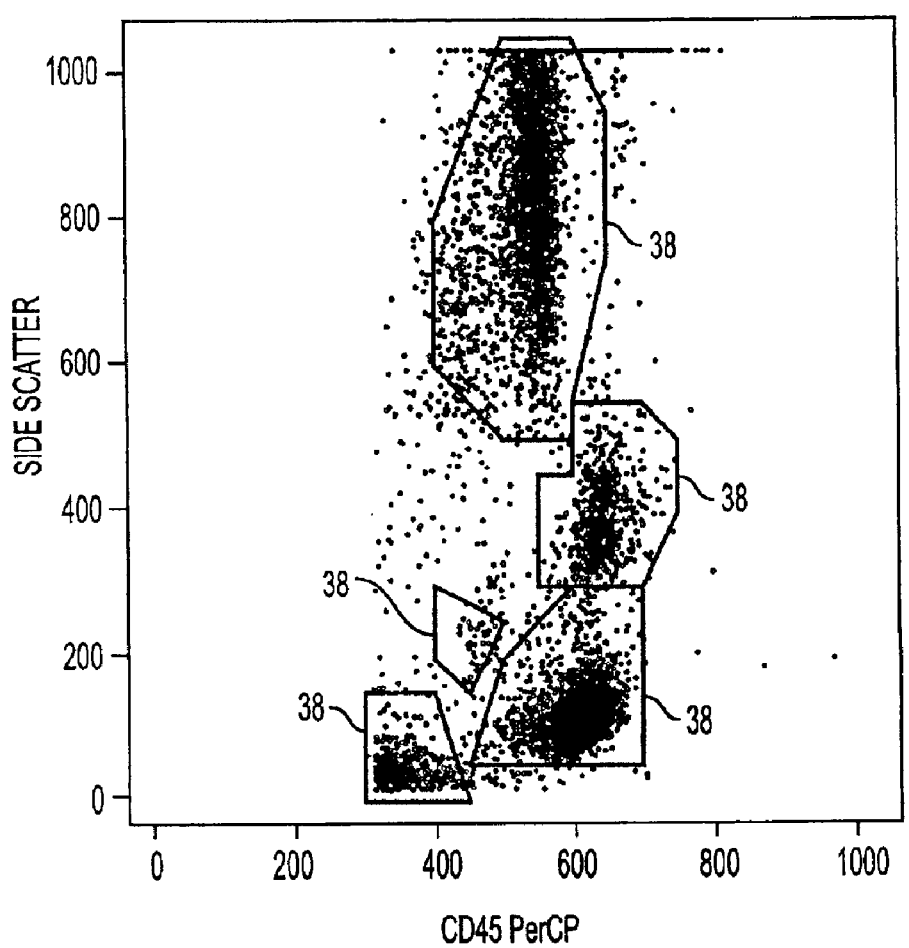
FIG. 11 shows the effect of line simplification applied to the cluster boundaries shown in FIG. 10 in accordance with an embodiment of the present invention.
Figure 12:
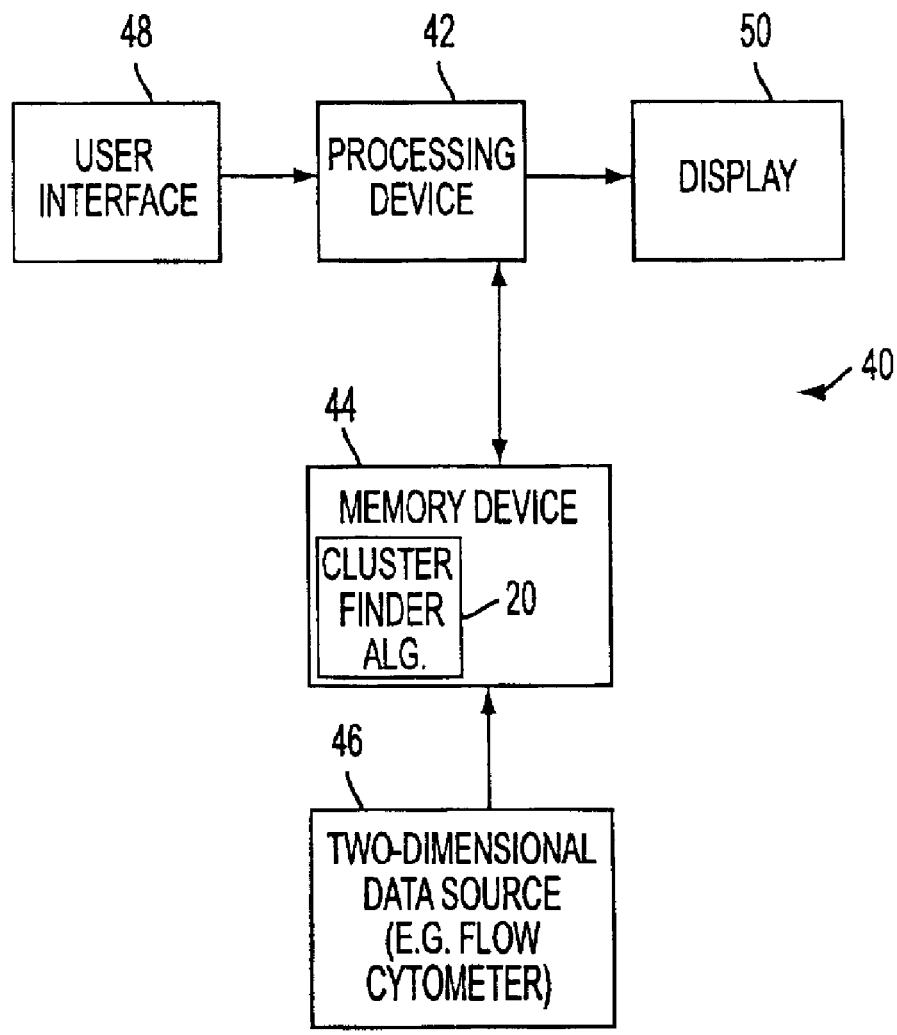
FIG. 12 is a block diagram of an apparatus constructed in accordance with an embodiment of the present invention.

The cluster finder algorithm 20 is preferably implemented in software code that is executed by a programmable digital computer (FIG. 12). The processing device implementing the cluster finder algorithm 20 can receive the data to be processed via an electronic file comprising a table having two columns of numbers corresponding to points (x,y) in the scatter plot, for example. An exemplary scatter plot is shown in FIG. 2. The exemplary data provided in FIG. 2 will be processed in accordance with the present invention and described below in connection with FIGS. 3–12 for illustrative purposes.

With reference to FIG. 1, the cluster finder algorithm 20 comprises the following steps:
1. Generate a two-dimensional density estimate from the data;
2. Locate clusters in the density estimate;
3. Determine boundaries around clusters; and
4. Simplify the cluster boundaries into manageable polygons.

Step 1. Generate a Two-dimensional Density Estimate from the Data

To use the cluster finder algorithm 20, a sample or data set is needed. As stated previously, the cluster finder algorithm 20 operates with two-dimensional data of size n, that is, a sample of n pairs of points: $(x_i, y_i)$, i=1, . . . , n. Such data are typically displayed in a two-dimensional scatter plot such as that depicted in FIG. 2.

Figure 3:
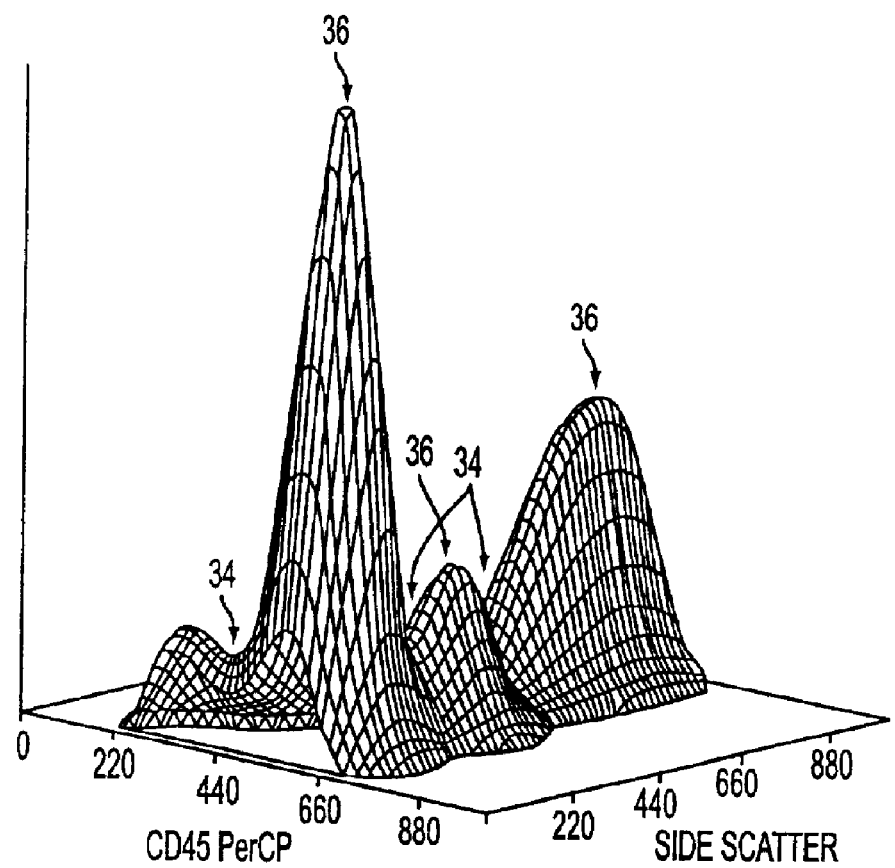
FIG. 3 is a three-dimensional plot of a density estimate of the scatter plot in FIG. 2 obtained via processing in accordance with an embodiment of the present invention.

As indicated by block 22 in FIG. 1, the algorithm 20 commences with the generation of a two-dimensional density estimate from the data. A density estimate is an estimate of the typically unknown probability density function from which the data were generated. A density estimate adds a third dimension, z, to the two-dimensional data whereby the value of z varies with the frequency or density of the (x, y) data pairs. The resulting density estimate can be visualized in a three-dimensional plot as shown in FIG. 3. The peaks in the graph of FIG. 3 correspond to high values of z and are located in areas where there is a high frequency of (x, y) data pairs. The valleys and low, flat areas in the graph of FIG. 3, that is, the places where z is low, correspond to places where (x, y) data pairs are sparse.

While the theory and mechanics of density estimation are generally known, the cluster finder algorithm 20 preferably employs a Gaussian kernel estimator. In addition, the implementation of the Gaussian kernel estimator in accordance with the present invention is quite different from its conventional use. In accordance with an aspect of the present invention, the data (e.g., in the scatter plot of FIG. 2) is first "binned" to create a two-dimensional histogram of the data before creating the smooth density estimate. This aspect of the step illustrated at block 22 in FIG. 1 significantly decreases the execution time of the algorithm 20, allowing it to function with real-time feedback to the user.

Figure 4:
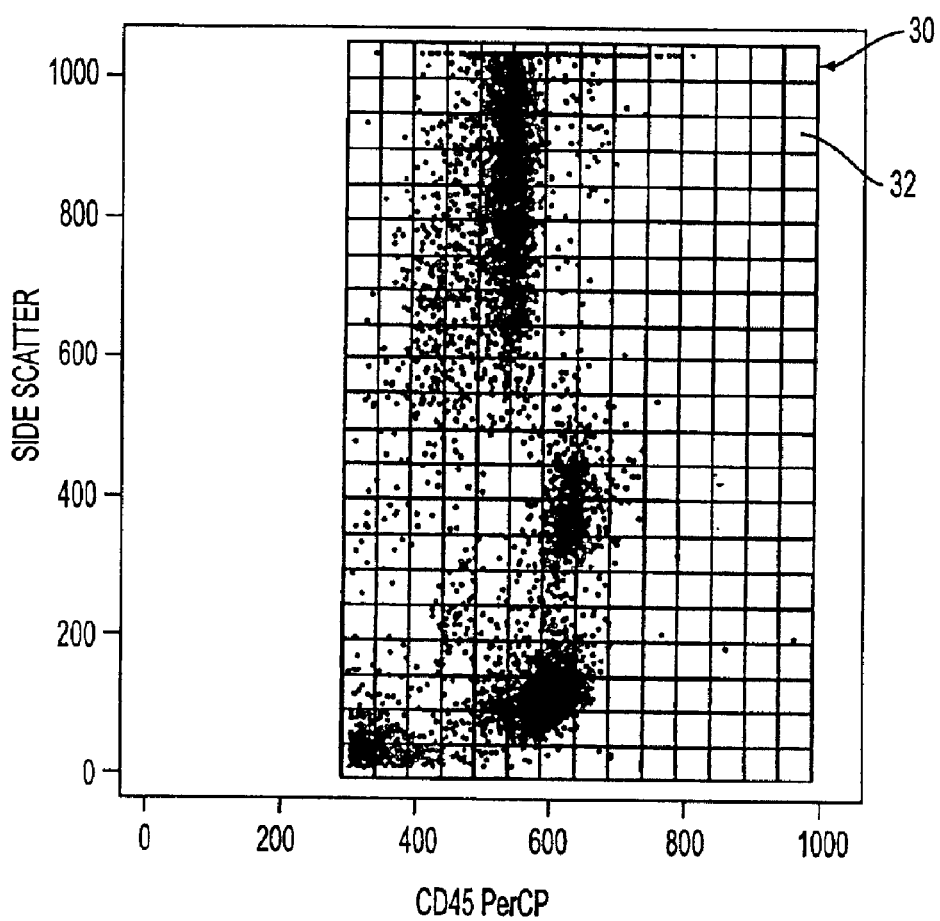
FIG. 4 depicts a grid provided on the scatter plot of FIG. 2 in accordance with an embodiment of the present invention.
Figure 5:
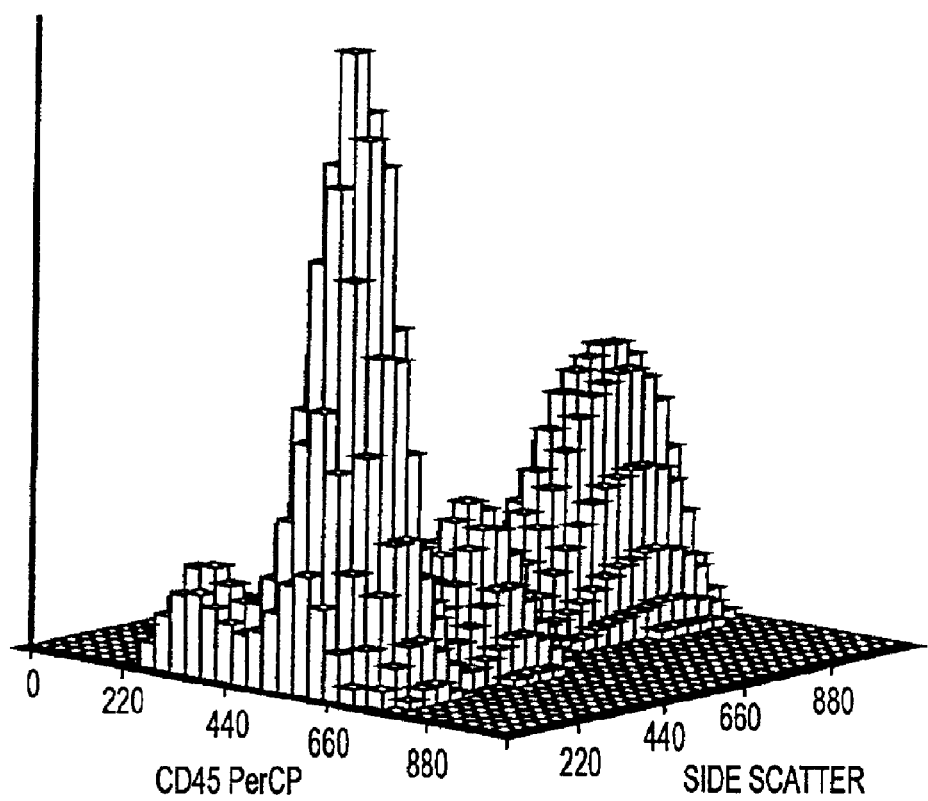
FIG. 5 is a two-dimensional histogram of the data from the scatter plot of FIG. 2.
Figure 6:
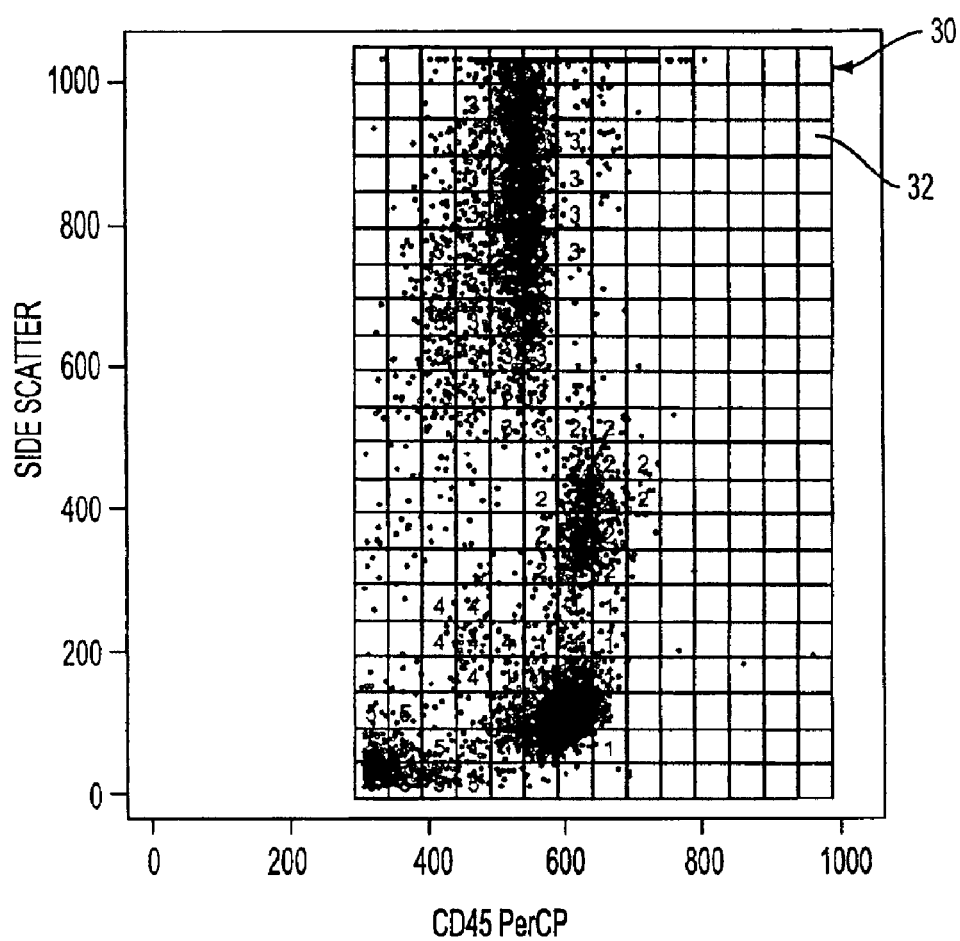
FIG. 6 depicts a labeled grid provided on the scatter plot of FIG. 2 to indicate cluster membership in accordance with an embodiment of the present invention.

To create a two-dimensional histogram, a grid 30 is constructed in the x-y plane that spans the range of the data, as illustrated in FIG. 4. The grid 30 can have a different number of divisions or bins 32 in the x direction than it has y direction; that is, the grid has m bins in the x direction and p bins in the y direction. The number of data points that fall into each of the m×p bins is then counted. The bin locations and the resulting counts comprise a two-dimensional histogram and are usually visualized in a graph like that shown in FIG. 5.

Binning the data is advantageous because it increases the speed of the algorithm by reducing the number of steps needed to create the density estimate. Most density estimation methods employ numerous operations on every point in the data set. This can be a significant burden when analyzing flow cytometry samples since these data sets typically contain tens of thousands of points and often exceed 100,000 points. The density estimation method of the present invention preferably operates only on the m×p histogram bin counts, that is, a number that stays fixed even as sample size increases. For example, if, for illustrative purposes, m=p= 64, then density estimation in accordance with the present invention employs operations on 64×64=4096 bin counts even though samples may contain hundreds of thousands of data points.

Once the data have been binned into a two-dimensional histogram, the Gaussian filter algorithm can be applied to the bin counts to obtain a smooth density estimate. While other routines such as a Fast Fourier Transform (FFT) can be used, a Gaussian filter algorithm such as the algorithm proposed by Ian T. Young and Lucas J. van Vliet in the article "Recursive Implementation of the Gaussian Filter in Signal Processing" 44:139–151 (1995), the disclosure of which is hereby incorporated by reference, is preferred since it is faster than any competitive methods. The filter is applied to the bin counts of each row of the two-dimensional histogram producing a smoothed version of the histogram shown in FIG. 5. Details of the filter equations are provided below after the steps of the algorithm 20 have been described.

Step 2. Locate Clusters in the Density Estimate

In this step, which is illustrated at block 24 in FIG. 1, the x,y data plane is divided into mutually exclusive regions or clusters according to the height of the density estimate obtained in Step 1 (block 22). Recall that in Step 1, the density estimate was created with and evaluated on an m×p grid. In Step 2 (block 24), each bin of the grid is assigned to a cluster. For example, all of the bins 32 in FIG. 6 that are labeled with the number 1 have been assigned to the same cluster and likewise for the other numbered bins in FIG. 6. It is to be understood that all of the bins are assigned to a cluster, but only the most prominent clusters are labeled in FIG. 6 for clarity.

Assigning cluster membership to the grid bins 32 is accomplished using a modified version of an algorithm described in Koonst, W. L. G., and Fukunaga, K., "A Nonparametric Valley-Seeking Technique for Cluster Analysis," *IEEE Transactions on Computers* 21(2): 171–178 (1972) (hereinafter referred to as Koonst and Fukunaga's algorithm), the disclosure of which is hereby incorporated by reference, in accordance with an aspect of the present invention. Koonst and Fukunaga's algorithm assumes no particular structure to the points at which the density estimate has been evaluated and is therefore a rather slow algorithm that would be impractical for more than a few thousand data points. The modifications in accordance with the present invention that are described herein have been made to maximize the advantages rendered via the grid structure imposed on the data in Step 1. The modifications used in accordance with the present invention significantly improve the execution speed of Koonst and Fukunaga's algorithm and allow the clustering to take place extremely quickly even on very large data sets.

Figure 7:
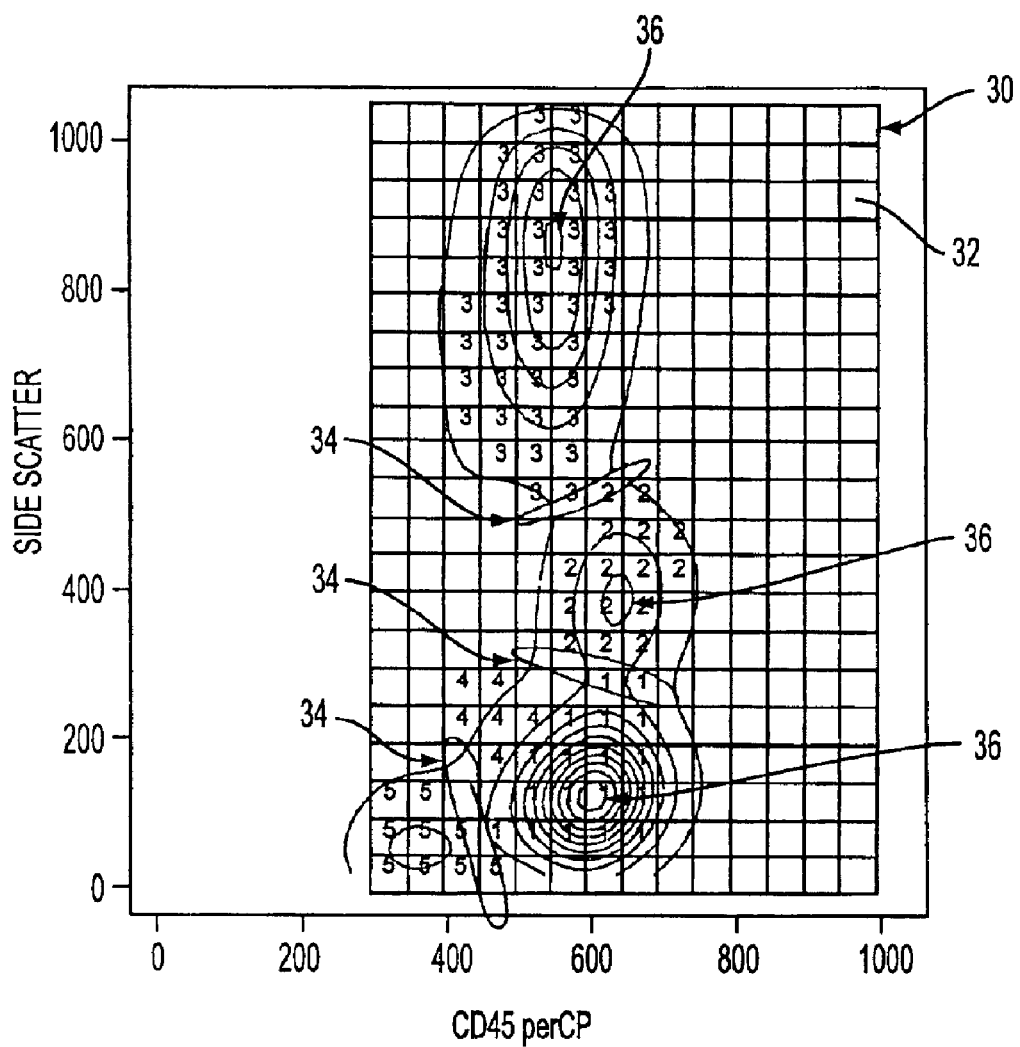
FIG. 7 is a contour plot of the scatter plot of FIG. 2 in accordance with an embodiment of the present invention.
Figure 8:
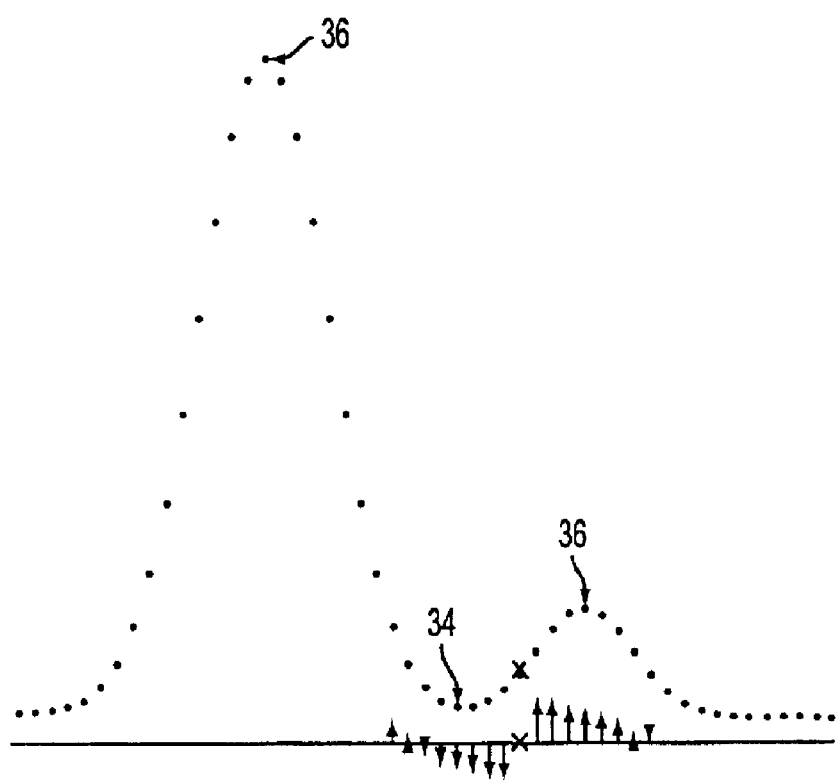
FIGS. 8 and 9 are graphs illustrating assignment of cluster membership in accordance with an embodiment of the present invention.

A "good" clustering involves associating bins that are separated from other clusters by a valley indicated generally at 34 in the density estimate of FIGS. 3 and 7. For example, the boundary between bins assigned to cluster 2 in FIG. 7 and those assigned to cluster 3 is aligned with a valley 34 in the density estimate. The same is true for the other clusters which suggests that the clustering shown in FIG. 7 is good.

Figure 9:
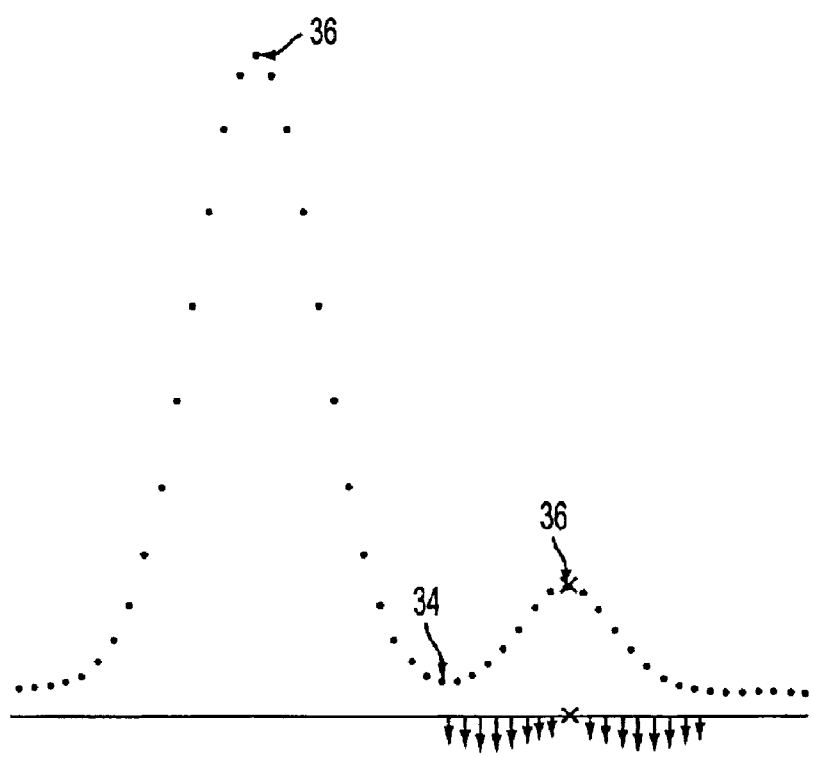

Finding the valleys in a density estimate is a relatively trivial task in one-dimensional data, but becomes more complicated in data sets of two or more dimensions. In accordance with the present invention, this task is accomplished by linking data points to neighboring points that are "uphill" from them. In other words, for each point in the data set, $(x_i, y_i)$, the algorithm 20 looks at the height of the density estimate evaluated at each of the point's neighbors, that is, at all of the other points that are within some radius, r, of $(x_i, y_i)$. Let $S = \{x_j, y_j\}, j=1, \ldots s$, be the set of all of the points within a radius, r, of $(x_i, y_i)$. Next, calculate the gradient of the density estimate between the density estimate evaluated at each point in S and the density estimate evaluated at the point $(x_i, y_i)$:

$$g_j = \frac{z_j - z_i}{\sqrt{(x_j - x_i)^2 + (y_j - y_i)^2}}, j = 1, \ldots s,$$

where $z_k$ is the height of the density estimate evaluated at $(x_k, y_k)$. Then, $(x_i, y_i)$ is linked to the point in S which has the highest, positive value of g. In other words, $(x_i, y_i)$ is linked to whichever point in its neighborhood is the farthest uphill according to the density estimate. Points that have no neighbors uphill from them are at the tops of local peaks (indicated generally at 36 in FIGS. 3 and 7) in the density estimate and they will not be linked to any other points To illustrate this approach, consider the one-dimensional example illustrated in FIG. 8. The dots represent the height of a density estimate evaluated at a series of one-dimensional points. To assign the point marked with an x to a cluster, the algorithm 20 looks at a set of points to either side. The arrows represent the gradient to each of the points in the neighborhood. Upward arrows correspond to positive gradients and the length of the arrow is proportional to the magnitude of the gradient. The point marked with x is linked to the point directly to its right since that point has the largest positive gradient. In this case, the algorithm 20 leads to the proper result. Point x is associated with another point to the right of the valley 34 in the density estimate. A second example is provided illustrated in FIG. 9. In FIG. 9, the point x has no neighbors with a positive gradient since there is a local peak 36 in the density estimate centered at x. Thus, point x becomes a root meaning that other points may be linked to it, but has no uphill link to any other point.

As noted above, Koonst and Fukunaga's basic algorithm has been modified in accordance with the present invention to exploit the advantages of the grid structure imposed on the data and density estimate in Step 1. The main difference between the present invention and Koonst and Fukunaga's basic algorithm is that, with regard to the present invention, the neighbors of any point in a grid are known since they are fixed in space. In Koonst and Fukunaga's more generic approach, on the other hand, the neighbors of every point must be found through a search mechanism. This requirement is computationally prohibitive for large data sets. A second difference is that Koonst and Fukunaga's algorithm assigns cluster labels to each point in the data set, while the present invention only assigns labels to the bins in the grid. Again, this results in an improvement in computational efficiency for large data sets. For example, with a sample of 100,000 data points, Koonst and Fukunaga's approach assigns labels to each of the 100,000 points, while the algorithm of the present invention assigns labels to only the 64×64=4096 bins in the grid. A preferred embodiment for cluster assignment step (block 24 in FIG. 1) is described below following the description of all of the steps of the algorithm 20.

Step 3. Determine Boundaries around Clusters

The method of determining boundary nodes for each cluster will now be described. For each grid point or bin 32 with a particular cluster label, all other nodes with the same label are examined to determine if the grid point in question is an interior point or a boundary point. An interior point has a neighbor grid point with the same cluster label on all sides, while an exterior point has one or more neighbor grid points with a different or no cluster label.

Figure 10:
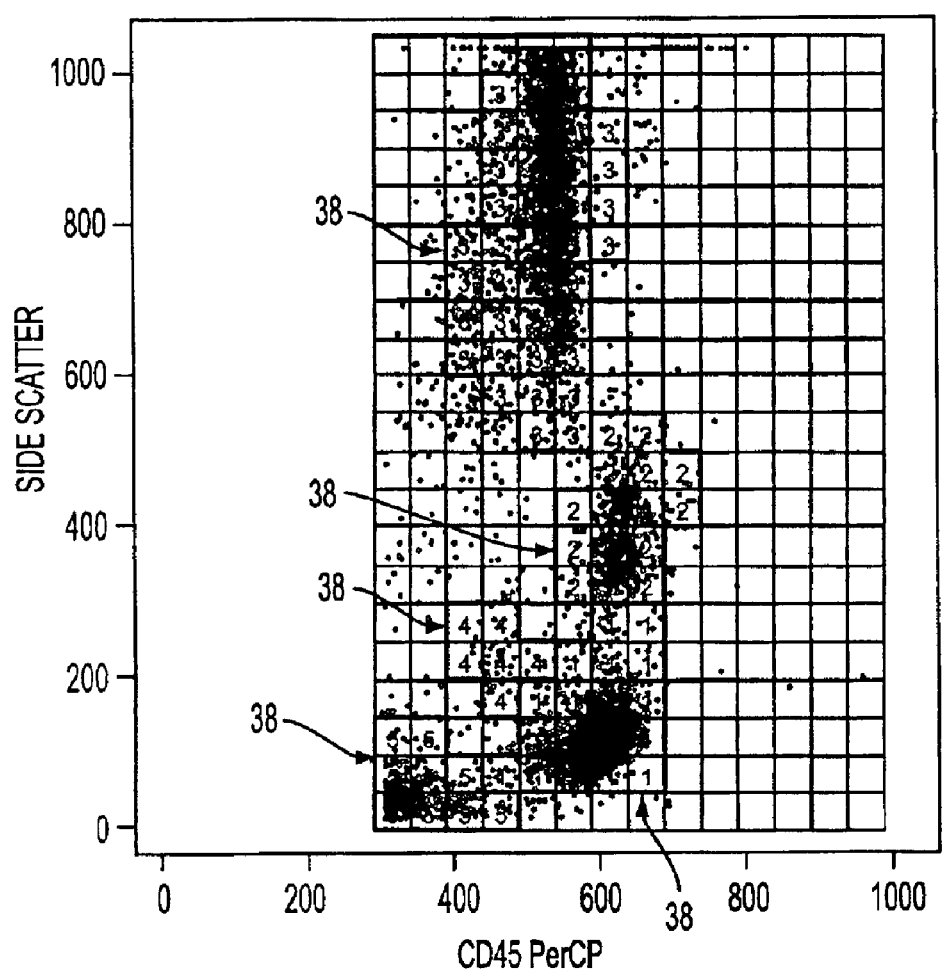
FIG. 10 depicts polygonal boundaries encompassing the clusters shown in FIG. 7 in accordance with an embodiment of the present invention.

The cluster boundary points determined above do not necessarily define the boundary in a clear, geometric manner. In accordance with the present invention, they are resequenced to form a continuously defined boundary, as illustrated in FIG. 10. This task has been performed by others using conventional, general numerical methods such as simulated annealing as described in W. H. Press, S. A. Teukolsky, W. T. Vetterling, and B. P. Flannery, "Numerical Recipes in Fortran, Second Edition", Cambridge University Press, 436–448 (1992), the disclosure of which is hereby incorporated by reference. These general processes, however, are highly inefficient for the implementation of the present invention.

The algorithm 20 of the present invention takes advantage of the binned nature of the density estimate described above in connection with Step 1. The algorithm 20 proceeds systematically, bin by bin, along the grid described, for example, with reference to FIG. 4. For each boundary point, a table of neighboring boundary points is first established. As the algorithm 20 proceeds, table is examined to determine the path to take along the bins of the grid.

The majority of the points that get processed have only two neighbors. In this case, examination of the table is a simple decision process. However, the process can become more complicated when a point has more than two neighbors. For that point, one of the neighbors is arbitrarily chosen, and the process carries on to the end. At the end, the table is reviewed to ascertain if any points have been missed. If not, the algorithm 20 proceeds to the next cluster; otherwise, the algorithm 20 goes back and selects a different, but not previously tried, point at the multiple choice point, and carries the process through again to the end. This process is continued until a satisfactory result has been achieved, e.g., missing only a predetermined fraction of boundary points in the final traversal. As mentioned earlier, the algorithm 20 is significantly faster in terms of processing time than the general numerical methods that have been traditionally utilized, such as simulated annealing.

Step 4. Simplify the Cluster Boundaries into Manageable Polygons

As can be seen in FIG. 10, the boundaries 38 that were determined in Step 3 follow the outlines of the bins 32 in the data grid 30. This means that boundaries tend to be jagged, like a ladder with many small steps. Also, since the decisions described in Step 3 are made systematically across the grid on a bin-by-bin basis, the boundaries contain at least one vertex for each bin it traverses. This typically results in boundaries with a large number of vertices, For or example, boundaries created on a 64×64 grid might contain dozens of vertices.

The purpose of Step 4 is to simplify the boundaries 38 created in Step 3 so that they employ fewer vertices to encompass roughly the same geometrical region. The line simplification technique developed by D. H Douglas and T. K. Peuker, "Algorithms for the Reduction of the Number of Points Required to Represent a Digitized Line or its Caricature", *The Canadian Cartographer* 10(2):112–122 (1973), the disclosure of which is hereby incorporated by reference, is preferably utilized to achieve this goal, although other techniques can be used. Researchers in the field of cartography have refined this based on the work of J. D. Whyatt and P. R. Wade entitled "The Douglas-Peuker Line Simplification Algorithm.", *Society of University Cartographers* (SUC) Bulletin, 22(1):17–25 (1988), the disclosure of which is hereby incorporated by reference.

FIG. 11 illustrates the result of the boundary simplification step. As shown in FIG. 11, the boundaries 38 are shaped more simply than those in FIG. 10, and they also contain fewer vertices. The small number of vertices makes it feasible for users to easily manipulate the boundaries produced by the algorithm 20. In other words, with a simple cluster boundary, a user need only manipulate one or two vertices to make significant adjustments to the shape of the cluster boundary. Conversely, if the cluster boundary is comprised of numerous vertices, the user would need to manipulate many more vertices to effect a significant change in the shape of the boundary.

Details of the Gaussian Filter used to Create the Smooth Density Estimate in Step 1

The algorithm used to implement a Gaussian filter was derived from the paper "Recursive implementation of the Gaussian filter", by Ian T. Young and Lucas J. van Vliet in *Signal Processing* 44 (1995) 139–151, the disclosure of which is hereby incorporated by reference.

This algorithm uses a recursive implementation of a Gaussian filter. The implementation is faster than other traditional methods such as Fast Fourier Transforms (FFTs), straightforward convolution of the discretized data with samples of a Gaussian density function, or multiple convolutions with a uniform filter kernel.

The following equations are used in the algorithm as described below:

Equation 1:

$$0.5 \leq \sigma < 2.5 \quad q = 3.97156 - 4.14554(1 - 0.26892\sigma)^{1/2}$$

$$\sigma \geq 2.5 \quad q = 0.98711\sigma - 0.96330$$

Equation 2:

$$b_0 = 1.57825 + 2.44413q + 1.4281q^2 + 0.422205q^3$$

$$b_1 = 2.44413q + 2.85619q^2 + 1.26661q^3$$

$$b_2 = 1.4281q^2 + 1.26661q^3$$

$$b_3 = 0.422205q^3$$

Equation 3—Normalization Constant:
Both forward and backward filters have the same normalization constant, B, where $$B = 1 - (b_1 + b_2 + b_3)/b_0.$$

The input data are first filtered in the forward direction as described in the difference equation 4. The output of this result (hereinafter referred to as w[n]) is then filtered in the backward direction according to the difference equation 5.

Equation 4—Forward Filter:

$$w[n] = B \text{ in}[n] + (b_1 w[n-1] + b_2 w[n-2] + b_3 w[n-3])/b_0$$

Equation 5—Backward Filter:

$$\text{out}[n] = B w[n] + (b_1 \text{ out}[n+1] + b_2 \text{ out}[n+2] + b_3 \text{ out}[n+3])/b_0$$

Once the target smoothing parameter, sigmas, is selected, a procedure is performed by the algorithm 20 to determine values for the five coefficients of the recursive filter. The procedure involves computational solution of closed-form algebraic equations, as follows, in the x and y dimensions. First, equation 1 is utilized to determine the coefficient q. Second, the values for coefficients $b_0$, $b_1$, $b_2$, and $b_3$ are computed by following equation 2. Third, B is determined by equation 3. At this point, all the filter coefficients have been determined, and the forward filter can be implemented with equation 4. Finally, the backward filter is implemented by utilizing equation 5. Once all of the above steps are executed, the desired, smoothed density estimate is obtained.

Finding Clusters in the Density Estimate in Step 2
Overview:
  A. Eliminate outliers in the density estimates
  B. Find all clusters in the histogram, labeling each bin with the ID of the cluster to which it belongs.
  C. Optionally eliminate minor clusters.
A. Eliminate Outliers:

Outliers are eliminated by zeroing out all bins where the density estimate is below a selected value CUTFRACT1 times the maximum value in the density estimate. The value used for CUTRACT1 can be determined experimentally and is preferably 0.03, although other values can be used. For example, the algorithm 20 can perform the following steps:
1) Iterate over all the bins in the density estimate to determine maxDensity, that is, the maximum density value in the histogram;
2) Compute the minimum density threshold, e.g., minThreshold=CUTFRACT1*maxDensity; and
3) Set to 0 any bin with a count less than minThreshold.

B. Find Clusters

The algorithm 20 can then perform the following steps:
1) Begin with a smooth density estimate evaluated on a grid;
2) Find the parent for each grid point using the steepest ascent algorithm:
  a) Note: Calculating the actual slope can a square root operation, the expense and time for which can be avoided because the algorithm 20 need only to determine if one slope is greater than another. Thus, if the square root is not taken, the necessary information is obtained by comparing the square of the slope;
  b) If the current node is not lower than any surrounding nodes, a determination is made as to whether the current node is the parent node; and
  c) If the current node is the parent node, this indicates that a new cluster has been found. The new cluster is assigned a cluster ID and marked as having no parent (parent ID=self);
3) Label each root with the ID of the cluster to which it belongs;
4) When all roots are located, give the same label to all points linked to a given root:
  a) For each node, get the ID of its parent node;
  b) Recursively find the ID of its parent node until a node is reached that has no parent (e.g., that node is the true peak of the cluster); and
  c) The label of that node as the cluster ID. Assign that cluster ID as the label of the current node.

C. Eliminate Minor Clusters(Optional)

Very small clusters can be optionally discarded to counteract the effects of white space and ripples in the density estimate (this may lead to some unclassified grid bins.) The algorithm 20 operates as follows:
1) Sort clusters by cumulative densities;
2) Calculate the total density of the density estimate;
3) Eliminate those clusters less than a selected value CUTFRACT2 of the total density, where the value of CUTFRACT2 can be determined previously by experimentation and is preferably 0.05; and
4) Relabel nodes (discard labels of clusters that were eliminated in the previous step).

Programmed Apparatus

With reference to FIG. 12, the cluster finder algorithm 20 can be implemented in a programmed apparatus 40 comprising a processing device 42 and a memory device 44. The sample of data points from a source 46 such as a flow cytometer can be stored, for example, in the memory device 44. The processing device 42 can be connected to a user interface 48 from which to receive user inputs and to a display 50. The display 50 can generate screens to provide a user with scatter plots, density estimates, as well as cluster and boundary information (e.g., as illustrated in FIGS. 2–7) generated in accordance with the algorithm 20. The display 50 can also generate screens to provide the user with menus and other screen options for selectively viewing the scatter plots and clusters. For example, the user can click on a cluster of points in a scatter plot, and the algorithm 20 can process and display the boundary around that particular cluster. The user can request the algorithm 20 to process and display the boundaries of all clusters it finds simultaneously. The user can change the parameter sigma described above in connection with the density estimate to make the boundaries more tight or loose.

Automated Data Analysis

The process described in the previous section was discussed in the context of processing a single data set. In a clinical or laboratory setting, however, multiple data sets often need to be processed in succession (e.g., via batch processing). Examples of when a batch process is appropriate include, but are not limited to: (i) a clinical trial where multiple samples from different donors need to be analyzed and compared; and (ii) research involving multiple measurements on the same sample to, for example, average the results into one overall assessment.

Unfortunately, gating of cluster populations in both of these scenarios is commonly done manually, that is, by hand. Gating data by hand is cumbersome, very time intensive, and often prone to error due to extreme variability of experience from technician to technician.

The present invention automates batch processing of multiple data sets in the following manner. The user first gates a single representative data file using the interactive process described in the previous section. The cluster finder algorithm 20 remembers the location of the representative gates as a template. This template is then used as a "seed" for the next data set that is to be analyzed. This scheme obviates the need for the user to manually use a pointing device again to select the locations (e.g., seed points) of the desired clusters in the next data set. The gates are then recomputed so as to be custom for the new data set, based on the trigger "seeds" of the previous data set. The clusters formed by the custom recomputation are then saved as a new analysis file. In a similar manner, the remaining data sets are automatically gated based on the initial template formed at the beginning of the batch run.

Utilizing this overall process, the present invention can gate an entire database of similarly obtained data in an automatic manner without any user interaction other than the initial gates selected by the user on the first representative data set. Accordingly, a significant increase in productivity is realized by a laboratory that utilizes the batch processing aspect of the present invention. Multiple templates can be developed for each assay that a primary investigator uses in his or her laboratory. Such action eliminates variability in gating style that may exist from technician to technician within the same laboratory. In addition, a technician would no longer need to be an expert in gating a particular assay, so long as the correct template was formed beforehand.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A method for identifying clusters in two-dimensional data, wherein said data comprises a plurality of clusters, comprising:
   generating a two-dimensional histogram characterized by a grid having an x-axis and a y-axis and a selected number of bins in the x-direction and a selected number of bins in the y-direction, said data comprising n pairs of points $(x_i, y_i)$, i=1, . . . ,n, said histogram comprising fewer bins than said points;
   determining a density estimate based on said bins, wherein said density estimate is characterized by a three-dimensional plot depicting peaks and valleys; and
   identifying at least one cluster in said data, said at least one cluster comprising a plurality of points which satisfy a selected density criteria.

2. A method as claimed in claim 1, wherein said determining step comprises generating a smoothed density estimate.

3. A method as claimed in claim 2, wherein said smoothed density estimate is generated using a Gaussian kernel estimator algorithm.

4. A method as claimed in claim 1, further comprising determining a boundary around said at least one cluster.

5. A method as claimed in claim 4, wherein said boundary is a polygon characterized by a plurality of vertices, and further comprising processing said boundary to reduce the number of said vertices while enclosing approximately the same area within said boundary.

6. A method as claimed in claim 1, wherein, said identifying step comprises locating valleys in said density estimate and identifying each of said plurality of clusters as being separated from the others by at least one of said valleys.

7. A method as claimed in claim 6, wherein said identifying step further comprises comparing the slope of each of said bins with that of adjacent ones of said bins.

8. A method as claimed in claim 7, wherein said identifying step further comprises:
   determining which of said bins correspond to respective peaks of said plurality of clusters using said slope;
   assigning said bins that correspond to said peaks with respective cluster identification codes; and
   assigning each of said bins associated with one of said peaks with the corresponding one of said cluster identification codes.

9. A method as claimed in claim 8, further comprising determining a boundary around said at least one cluster.

10. A method as claimed in claim 9, wherein said step of determining a boundary comprises analyzing each of said bins to determine if adjacent ones of said bins have the same one of said cluster identification codes, said bins being labeled as exterior points if they have no adjacent said bins with said data or the same one of said cluster identification codes.

11. A method as claimed in claim 10, wherein said boundary is a polygon characterized by a plurality of vertices, and further comprising processing said boundary to reduce the number of said vertices while enclosing approximately the same area within said boundary.

12. A method for identifying clusters in two-dimensional data, wherein said data comprises a plurality of clusters, comprising a plurality of points, the method comprising:
   generating a density estimate based on said data, wherein said density estimate is characterized by a three-dimensional plot depicting peaks and valleys;
   identifying at least one cluster in said data, said at least one cluster comprising a plurality of points which satisfy a selected density criteria; and
   determining a boundary around said at least one cluster.

13. A method as claimed in claim 12, wherein said generating step comprises generating a smoothed density estimate.

14. A method as claimed in claim 13, wherein said smoothed density estimate is generated using a Gaussian kernel estimator algorithm.

15. A method as claimed in claim 12, wherein said boundary is a polygon characterized by a plurality of vertices, and further comprising processing said boundary to reduce the number of said vertices while enclosing approximately the same area within said boundary.

16. A method as claimed in claim 12, wherein said data comprises n pairs of points $(x_i, y_i)$, i=1, . . . ,n, and said generating step comprises:
   generating a two-dimensional histogram, said histogram comprising fewer bins than said points; and
   determining said density estimate based on said bins.

17. An apparatus for identifying clusters in two-dimensional data, wherein said data comprises a plurality of clusters, comprising:
   a processing device; and
   a memory device coupled to said processing device for storing a cluster finder algorithm, said processing device being programmable in accordance with said cluster finder algorithm to generate a two-dimensional histogram characterized by a grid having an x-axis and a y-axis and a selected number of bins in the x-direction and a selected number of bins in the y-direction, said data comprising n pairs of points $(x_i, y_i)$, i=1, . . . ,n, said histogram comprising fewer bins than said points, to determine a density estimate based on said bins, wherein said density estimate is characterized by a three-dimensional plot depicting peaks and valleys, and to identify at least one cluster in said data, said at least one cluster comprising a plurality of points which satisfy a selected density criteria.

18. An apparatus as claimed in claim 17, wherein said processing device is programmable to generate a smoothed density estimate.

19. An apparatus as claimed in claim 18, wherein said processing device is programmable to implement a Gaussian kernel estimator algorithm to generate said smoothed density estimate.

20. An apparatus as claimed in claim 17, wherein said processing device is programmable to determine a boundary around said at least one cluster.

21. An apparatus as claimed in claim 20, wherein said boundary is a polygon characterized by a plurality of vertices, and said processing device is programmable process said boundary to reduce the number of said vertices while enclosing approximately the same area within said boundary.

22. An apparatus as claimed in claim 21, wherein said apparatus further comprises a user input device and a display connected to said processing device, said display providing a visual indication of said plurality of clusters, said processing device being operable to provide a user with said boundary of one of said plurality clusters when selected via said user input device.

23. An apparatus as claimed in claim 22, said processing device being operable to alter said boundary of at least one of said plurality clusters in response to user commands generated via said user input device.

24. An apparatus as claimed in claim 17, wherein said two-dimensional data represents a first data set and said processing device is operable to perform batch processing of a second data set, said processing device storing a template in said memory device corresponding to said at least one cluster in said first data set and using said template to facilitate location of clusters in said second data set.

25. An apparatus for identifying clusters in two-dimensional data, wherein said data comprises a plurality of clusters, comprising:

a processing device; and a memory device coupled to said processing device for storing a cluster finder algorithm, said processing device being programmable in accordance with said cluster finder algorithm to generate a density estimate based on said data, wherein said density estimate is characterized by a three-dimensional clot depicting peaks and valleys, identify at least one cluster in said data, said at least one cluster comprising a plurality of points which satisfy a selected density criteria, and determine a boundary around said at least one cluster.

26. An apparatus as claimed in claim 25, wherein said processing device is programmable to generate a smoothed density estimate.

27. An apparatus as claimed in claim 26, wherein said processing device is programmable to implement a Gaussian kernel estimator algorithm to generate said smoothed density estimate.

28. A method as claimed in claim 25, wherein said data comprises n pairs of points $(x_i, y_i)$, i=1, . . . ,n, and processing device is programmable to generate a two-dimensional histogram, said histogram comprising fewer bins than said points, and determine said density estimate based on said bins.

29. A computer program product for identifying clusters in two-dimensional data comprising a plurality of points, wherein said data comprises a plurality of clusters, the computer program product comprising:

a computer-readable medium; and a cluster finder module stored on said computer-readable medium that generates a density estimate based on said date, wherein said density estimate is characterized by a three-dimensional plot depicting peaks and valleys, identifies at least one cluster in said data, said at least one cluster comprising a plurality of points which satisfy a selected density criteria, and determines a boundary around said at least one cluster.

30. A computer program product as claimed in claim 29, wherein said cluster finder module generates a smoothed density estimate.

31. A computer program product as claimed in claim 30, wherein said smoothed density estimate is generated using a Gaussian kernel estimator algorithm.

32. A computer program product as claimed in claim 29, wherein said boundary is a polygon characterized by a plurality of vertices, said cluster finder module being operable to process said boundary to reduce the number of said vertices while enclosing approximately the same area within said boundary.

33. A computer program product as claimed in claim 29, wherein said data comprises n pairs of points $(x_i, y_i)$, i=1, . . . n, said cluster finder module being operable to generate a two-dimensional histogram, said histogram comprising fewer bins than said points, and to determine said density estimate based on said bins.

* * * * *

UNITED STATES PATENT AND TRADEMARK OFFICE
CERTIFICATE OF CORRECTION

PATENT NO. : 6,944,338 B2
DATED : September 13, 2005
INVENTOR(S) : Michael D. Lock, Sunil S. Dalal and Ilya Gluhovsky It is certified that error appears in the above-identified patent and that said Letters Patent is hereby corrected as shown below:

<u>Column 15,</u>
Line 17, delete "clot" and insert -- plot --.

Signed and Sealed this

Twenty-third Day of May, 2006

JON W. DUDAS
*Director of the United States Patent and Trademark Office*